United States Patent
Wraith et al.

(10) Patent No.: US 10,377,800 B2
(45) Date of Patent: *Aug. 13, 2019

(54) MYELIN OLIGODENDROCYTE GLYCOPROTEIN (MOG) PEPTIDE

(71) Applicant: APITOPE TECHNOLOGY (BRISTOL) LIMITED, Chepstow (GB)

(72) Inventors: David Wraith, Bristol (GB); Heather Streeter, Bristol (GB)

(73) Assignee: APITOPE TECHNOLOGY (BRISTOL) LIMITED, Chepstow (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/834,438

(22) Filed: Dec. 7, 2017

(65) Prior Publication Data

US 2018/0086802 A1 Mar. 29, 2018

Related U.S. Application Data

(63) Continuation of application No. 14/760,493, filed as application No. PCT/IB2014/058233 on Jan. 13, 2014, now Pat. No. 9,862,751.

(30) Foreign Application Priority Data

Jan. 15, 2013 (GB) .................................. 1300684.6

(51) Int. Cl.
C07K 14/47 (2006.01)
C07K 14/705 (2006.01)

(52) U.S. Cl.
CPC .... *C07K 14/4713* (2013.01); *C07K 14/70503* (2013.01); *C07K 2319/21* (2013.01)

(58) Field of Classification Search
None
See application file for complete search history.

(56) References Cited

U.S. PATENT DOCUMENTS

| | | | |
|---|---|---|---|
| 8,128,934 B2 | 3/2012 | Suzumura et al. | |
| 8,148,084 B2 | 4/2012 | O'Connor et al. | |
| 8,188,218 B2 | 5/2012 | Siahaan et al. | |
| 8,202,835 B2 | 6/2012 | Hillman | |
| 8,231,878 B2 | 7/2012 | Colonna et al. | |
| 8,263,064 B2 | 9/2012 | Karin et al. | |
| 8,293,468 B2 | 10/2012 | Prat et al. | |
| 9,862,751 B2 | 1/2018 | Wraith et al. | |
| 2005/0037422 A1 | 2/2005 | Ben-Nun et al. | |
| 2008/0103091 A1 | 5/2008 | Siahaan et al. | |
| 2008/0281001 A1 | 11/2008 | Wood et al. | |
| 2009/0048167 A1 | 2/2009 | Hillman | |
| 2009/0227018 A1 | 9/2009 | Watson et al. | |
| 2010/0003228 A1 | 1/2010 | Willimas et al. | |
| 2010/0003242 A1 | 1/2010 | Sabbadini et al. | |
| 2010/0310568 A1 | 12/2010 | Prat et al. | |
| 2011/0111395 A1 | 5/2011 | Saint-Remy | |
| 2011/0189178 A1 | 8/2011 | Desjarlais et al. | |
| 2012/0034696 A1 | 2/2012 | Wood et al. | |
| 2012/0045832 A1 | 2/2012 | Trapp et al. | |
| 2012/0058111 A1 | 3/2012 | Ehlers et al. | |
| 2012/0076808 A1 | 3/2012 | Wang et al. | |
| 2012/0077686 A1 | 3/2012 | Weiner et al. | |
| 2012/0082665 A1 | 4/2012 | Sabbadini | |
| 2012/0135016 A1 | 5/2012 | Eisenbach-Schwartz et al. | |
| 2012/0172297 A1 | 7/2012 | Ben-Nun et al. | |
| 2012/0177645 A1 | 7/2012 | Langermann et al. | |
| 2012/0195921 A1 | 8/2012 | Loftis et al. | |
| 2012/0230959 A1 | 9/2012 | Abbot et al. | |
| 2013/0236473 A1 | 9/2013 | Hirano et al. | |

FOREIGN PATENT DOCUMENTS

| | | |
|---|---|---|
| AU | 2010286351 A1 | 3/2012 |
| AU | 2010286361 A1 | 3/2012 |
| AU | 2012201067 A1 | 3/2012 |
| AU | 2012202713 A1 | 5/2012 |
| AU | 2012202776 A1 | 5/2012 |
| AU | 2006318791 B2 | 7/2012 |
| AU | 2011202900 B2 | 8/2012 |
| CA | 2492848 C | 1/2012 |
| CA | 2614171 C | 4/2012 |
| CA | 2363269 C | 6/2012 |
| CN | 102388307 A | 3/2012 |
| CN | 102666581 A | 9/2012 |
| CN | 102741279 A | 10/2012 |
| EA | 201070541 A1 | 12/2010 |
| EP | 1964574 A1 | 9/2008 |
| EP | 2233502 A1 | 9/2010 |
| EP | 2402022 A2 | 1/2012 |
| EP | 2411417 A1 | 2/2012 |
| EP | 2420833 A1 | 2/2012 |
| EP | 2431468 A1 | 3/2012 |
| EP | 1456380 B1 | 4/2012 |
| EP | 2436693 A2 | 4/2012 |
| EP | 2473521 A2 | 7/2012 |
| EP | 2473523 A2 | 7/2012 |
| EP | 1625148 B1 | 9/2012 |

(Continued)

OTHER PUBLICATIONS

Anderton et al., Influence of a dominant cryptic epitope on autoimmune T cell tolerance, Nat. Immunol., 3(2):175-81 (2002).

(Continued)

*Primary Examiner* — John D Ulm
(74) *Attorney, Agent, or Firm* — Marshall, Gerstein & Borun LLP

(57) ABSTRACT

There is provided a peptide which is capable of binding to an MHC molecule in vitro and being presented to a T cell without antigen processing (i.e. an apitope) which peptide comprises a portion of the region 40-60 of myelin oligodendrocyte glycoprotein (MOG). In particular there is provided an apitope which is selected from the following myelin oligodendrocyte glycoprotein peptides: MOG 41-55, 43-57, 44-58 and 45-59. There is also provided the use of such a peptide in a pharmaceutical composition and a method to treat and/or prevent a disease using such a peptide.

1 Claim, 7 Drawing Sheets

Specification includes a Sequence Listing.

(56) References Cited

FOREIGN PATENT DOCUMENTS

| | | |
|---|---|---|
| EP | 2500438 A2 | 9/2012 |
| EP | 1991259 B1 | 10/2012 |
| EP | 2510948 A1 | 10/2012 |
| IL | 185932 A | 2/2014 |
| IN | 433/CHENP/2010 | 7/2010 |
| IN | 251127 | 3/2012 |
| JP | 2012506451 A | 3/2012 |
| JP | 2012506453 A | 3/2012 |
| JP | 2012508865 A | 4/2012 |
| JP | 5010798 B2 | 8/2012 |
| JP | 2012162545 A | 8/2012 |
| NZ | 572644 A | 6/2012 |
| RU | 2441067 C2 | 1/2012 |
| WO | WO-95/06727 A2 | 3/1995 |
| WO | WO-95/07096 A1 | 3/1995 |
| WO | WO-97/35879 A1 | 10/1997 |
| WO | WO-99/12966 A1 | 3/1999 |
| WO | WO-00/11027 A1 | 3/2000 |
| WO | WO-01/031037 A2 | 5/2001 |
| WO | WO-01/072325 A1 | 10/2001 |
| WO | WO-02/16410 A2 | 2/2002 |
| WO | WO-03/029276 A2 | 4/2003 |
| WO | WO-03/037368 A2 | 5/2003 |
| WO | WO-2004/104026 A1 | 12/2004 |
| WO | WO-2005/044982 A2 | 5/2005 |
| WO | WO-2006/057003 A2 | 6/2006 |
| WO | WO-2006/097914 A2 | 9/2006 |
| WO | WO-2007/039552 A1 | 4/2007 |
| WO | WO-2007/055378 A1 | 5/2007 |
| WO | WO-2007/061805 A2 | 5/2007 |
| WO | WO-2007/094003 A2 | 8/2007 |
| WO | WO-2007/096396 A2 | 8/2007 |
| WO | WO-2007/131210 A2 | 11/2007 |
| WO | WO-2007/149982 A2 | 12/2007 |
| WO | WO-2008/055059 A2 | 5/2008 |
| WO | WO-2008/070344 A2 | 6/2008 |
| WO | WO-2008/149354 A2 | 12/2008 |
| WO | WO-2009/050283 A1 | 4/2009 |
| WO | WO-2009/056833 A2 | 5/2009 |
| WO | WO-2010/045265 A1 | 4/2010 |
| WO | WO-2010/055510 A2 | 5/2010 |
| WO | WO-2010/109010 A1 | 9/2010 |
| WO | WO-2010/126908 A1 | 11/2010 |
| WO | WO-2011/071059 A1 | 6/2011 |
| WO | WO-2011/097527 A2 | 8/2011 |
| WO | WO-2012/017439 A2 | 2/2012 |
| WO | WO-2012/019041 A2 | 2/2012 |
| WO | WO-2012/021856 A1 | 2/2012 |
| WO | WO-2012/031258 A1 | 3/2012 |
| WO | WO-2012/036214 A1 | 3/2012 |
| WO | WO-2012/041867 A2 | 4/2012 |
| WO | WO-2012/045324 A1 | 4/2012 |
| WO | WO-2012/056407 A1 | 5/2012 |
| WO | WO-2012/092485 A1 | 7/2012 |
| WO | WO-2012/103365 A1 | 8/2012 |
| WO | WO-2012/117076 A2 | 9/2012 |
| WO | WO-2014/041867 A1 | 3/2014 |

OTHER PUBLICATIONS

Brunmark et al., The new orally active immunoregulator laquinimod (ABR-215062) effectively inhibits development and relapses of experimental autoimmune encephalomyelitis, J. Neuroimmunol., 130(1-2):163-72 (2002).

Fujino et al., Amelioration of experimental autoimmune encephalomyelitis in Lewis rats by FTY720 treatment, J. Pharmacol. Exp. Ther., 305(1):70-7 (2003).

Hughes et al., Cross-reactivity between related sequences found in *Acinetobacter* sp., *Pseudomonas aeruginosa*, myelin basic protein and myelin oligodendrocyte glycoprotein in multiple sclerosis, J. Neuroimmunol., 144(1-2):105-15 (2003).

Counterpart Japanese Patent Application No. 2015-552188, Decision of Patent, dated Apr. 3, 2018.

Jonuleit et al., Induction of interleukin 10-producing, nonproliferating CD4(+) T cells with regulatory properties by repetitive stimulation with allogeneic immature human dendritic cells, J. Exp. Med., 192(9):1213-22 (2000).

Koffeman et al., Epitope-specific immunotherapy of rheumatoid arthritis: clinical responsiveness occurs with immune deviation and relies on the expression of a cluster of molecules associated with T cell tolerance in a double-blind, placebo-controlled, pilot phase II trial, Arthritis Rheum., 60(11):3207-16 (2009).

Muller et al., Spliceosomal peptide P140 for immunotherapy of systemic lupus erythematosus: results of an early phase II clinical trial, Arthritis Rheum., 58(12):3873-83 (2008).

Norman et al., Treatment of cat allergy with T-cell reactive peptides, Am. J. Respir. Crit. Care Med., 154(6 Pt. 1):1623-8 (1996).

Oldfield et al., Effect of T-cell peptides derived from Fel d 1 on allergic reactions and cytokine production in patients sensitive to cats: a randomised controlled trial, Lancet, 360(9326):47-53 (2002).

Counterpart Russian Patent Application No. 2015134356/10(052756), Office Action and Search Report, dated Dec. 11, 2017.

Schilling et al., Fumaric acid esters are effective in chronic experimental autoimmune encephalomyelitis and suppress macrophage infiltration, Clin. Exp. Immunol., 145(1):101-7 (2006).

Steinman et al., How to successfully apply animal studies in experimental allergic encephalomyelitis to research on multiple sclerosis, Ann. Neurol., 60(1):12-21 (2006).

Streeter et al., ATX-MX1467, a thereapeutic peptide vaccine for treatment of multiple sclerosis, Multiple Sclerosis, Abstract P533, 14:S29-293 (2008).

Streeter et al., Preclinical development and first-in-human study of ATX-MS-1467 for immunotherapy of MS, Neurol. Neuroimmunol. Neuroinflamm., 2(3):e93 (2015).

Tarzi et al., Induction of interleukin-10 and suppressor of cytokine signalling-3 gene expression following peptide immunotherapy, Clin. Exp. Allergy, 36(4):465-74 (2006).

Teitelbaum et al., Suppression of experimental allergic encephalomyelitis by a synthetic polypeptide, Eur. J. Immunol., 1(4):242-8 (1971).

Thrower et al., Proinsulin peptide immunotherapy in type 1 diabetes: report of a first-in-man Phase I safety study, Clin. Exp. Immunol., 155(2):156-65 (2009).

Warren et al., Intravenous synthetic peptide MBP8298 delayed disease progression in an HLA Class II-defined cohort of patients with progressive multiple sclerosis: results of a 24-month double-blind placebo-controlled clinical trial and 5 years of follow-up treatment, Eur. J. Neurol., 13(8):887-95 (2006).

Webb et al., Sphingosine 1-phosphate receptor agonists attenuate relapsing-remitting experimental autoimmune encephalitis in SJL mice, J. Neuroimmunol., 153(1-2):108-21 (2004).

Yang et al., Laquinimod (ABR-215062) suppresses the development of experimental autoimmune encephalomyelitis, modulates the Th1/Th2 balance and induces the Th3 cytokine TGF-beta in Lewis rats, J. Neuroimmunol., 156(1-2):3-9 (2004).

Yednock et al., Prevention of experimental autoimmune encephalomyelitis by antibodies against $\alpha 4\beta 1$ integrin, Nature, 356:63-66 (1992).

Yu et al., Interferon-beta inhibits progression of relapsing-remitting experimental autoimmune encephalomyelitis, J. Neuroimmunol., 64(1):91-100 (1996).

't Hart et al., Modelling of multiple sclerosis: lessons learned in a non-human primate, Lancet Neurol., 3(19):588-97 (2004).

Akdis et al., Role of interleukin 10 in specific immunotherapy, J. Clin. Invest., 102(1):98-106 (1998).

Anderton et al., Hierarchy in the ability of T cell epitopes to induce peripheral tolerance to antigens from myelin, Eur. J. Immunol., 28(4):1251-61 (1998).

Anderton et al., Mechanisms of central and peripheral T-cell tolerance: lessons from experimental models of multiple sclerosis, Immunol. Rev., 169:123-37 (1999).

Behan et al., The sad plight of multiple sclerosis research (low on fact, high on fiction): critical data to support it being a neurocristopathy, Inflammopharmacology, 18(6):265-90 (2010).

(56) References Cited

OTHER PUBLICATIONS

Burkhart et al., Peptide-induced T cell regulation of experimental autoimmune encephalomyelitis: a role for IL-10, Int. Immunol., 11(10):1625-34 (1999).

Fairchild et al., The nature of cryptic epitopes within the self-antigen myelin basic protein, Int. Immunol., 8(7):1035-43 (1996).

Greer et al., Correlation of blood T cell and antibody reactivity to myelin proteins with HLA type and lesion localization in multiple sclerosis, J. Immunol., 180(9):6402-10 (2008).

International Preliminary Report on Patentability, International Application No. PCT/IB2014/058233, dated Jul. 21, 2015.

International Search Report and Written Opinion, International Application No. PCT/IB2014/058233, dated Jul. 11, 2014.

Leadbetter et al., Experimental autoimmune encephalomyelitis induced with a combination of myelin basic protein and myelin oligodendrocyte glycoprotein is ameliorated by administration of a single myelin basic protein peptide. J. Immunol. 161: 504-12 (1998).

Leech et al., Recognition of a high affinity MHC class I-restricted epitope of myelin oligodendrocyte glycoprotein by CD8? T cells derived from autoantigen-deficient mice, Front Immunol., 2:17 (2011).

Liu et al., Affinity for class II MHC determines the extent to which soluble peptides tolerize autoreactive T cells in naive and primed adult mice—implications for autoimmunity, Int. Immunol., 7(8):1255-63 (1995).

Madsen et al., A humanized model for multiple sclerosis using HLA-DR2 and a human T-cell receptor, Nature Genet., 23:343-7 (1999).

McFarlin et al., Multiple sclerosis (first of two parts), N. Engl. J. Med., 307(19):1183-8 (1982).

McFarlin et al., Multiple sclerosis (second of two parts), N. Engl. J. Med., 307(20):1246-51 (1982).

Metzler et al., Inhibition of experimental autoimmune encephalomyelitis by inhalation but not oral administration of the encephalitogenic peptide: influence of MHC binding affinity, Int. Immunol., 5(9):1159-65 (1993).

Metzler et al., Inhibition of T-cell responsiveness by nasal peptide administration: influence of the thymus and differential recovery of T-cell-dependent functions, Immunology, 97(2):257-63 (1999).

Muller et al., Successful immunotherapy with T-cell epitope peptides of bee venom phospholipase A2 induces specific T-cell anergy in patients allergic to bee venom, J. Allergy Clin. Immunol., 101(6 Pt 1):747-54 (1998).

Ransohoff, Animal models of multiple sclerosis: the good, the bad and the bottom line, Nat. Neurosci., 15(8):1074-7 (2012).

Roberge et al., A Strategy for a Convergent Synthesis of N-Linked Glycopeptides on a Solid Support, Science, 269:202-4 (1995).

Summers et al., Phenotypic characterization of five dendritic cell subsets in human tonsils, Am. J. Pathol., 159(1):285-95 (2001).

Werkerle et al., Animal models of multiple sclerosis, Drug Discovery Today: Disease Models, 3(4):359-67 (2006).

Apitope Product Pipeline, Apitope, downloaded from the Internet at <http://www.apitope.com/pipeline/index.html> Accessed May 10, 2012 (2010), 2 pages.

Chinese Patent Application No. 201480009521.1, First Office Action, dated Aug. 11, 2017, 6 pg.

Great Britain Patent Application No. GB1200624.3, Search Report, dated May 18, 2012, 5 pg.

Smith et al., Epitope spread is not critical for the relapse and progression of MOG 8-21 induced EAE in Biozzi ABH mice, J. Neuroimmunol., 164(1-2):76-84 (Jul. 2005).

SEQUENCE LISTING

```
<160> NUMBER OF SEQ ID NOS: 8

<210> SEQ ID NO 1
<211> LENGTH: 15
<212> TYPE: PRT
<213> ORGANISM: Homo sapiens

<400> SEQUENCE: 1

Arg Pro Pro Phe Ser Arg Val Val His Leu Tyr Arg Asn Gly Lys
1               5                   10                  15

<210> SEQ ID NO 2
<211> LENGTH: 15
<212> TYPE: PRT
<213> ORGANISM: Homo sapiens

<400> SEQUENCE: 2

Pro Phe Ser Arg Val Val His Leu Tyr Arg Asn Gly Lys Asp Gln
1               5                   10                  15

<210> SEQ ID NO 3
<211> LENGTH: 15
<212> TYPE: PRT
<213> ORGANISM: Homo sapiens

<400> SEQUENCE: 3

Phe Ser Arg Val Val His Leu Tyr Arg Asn Gly Lys Asp Gln Asp
1               5                   10                  15

<210> SEQ ID NO 4
<211> LENGTH: 15
<212> TYPE: PRT
<213> ORGANISM: Homo sapiens

<400> SEQUENCE: 4

Ser Arg Val Val His Leu Tyr Arg Asn Gly Lys Asp Gln Asp Gly
1               5                   10                  15

<210> SEQ ID NO 5
<211> LENGTH: 218
<212> TYPE: PRT
<213> ORGANISM: Homo sapiens

<400> SEQUENCE: 5

Gly Gln Phe Arg Val Ile Gly Pro Arg His Pro Ile Arg Ala Leu Val
1               5                   10                  15

Gly Asp Glu Val Glu Leu Pro Cys Arg Ile Ser Pro Gly Lys Asn Ala
            20                  25                  30
```

```
Thr Gly Met Glu Val Gly Trp Tyr Arg Pro Pro Phe Ser Arg Val Val
        35                  40                  45

His Leu Tyr Arg Asn Gly Lys Asp Gln Asp Gly Asp Gln Ala Pro Glu
    50                  55                  60

Tyr Arg Gly Arg Thr Glu Leu Leu Lys Asp Ala Ile Gly Glu Gly Lys
65                  70                  75                  80

Val Thr Leu Arg Ile Arg Asn Val Arg Phe Ser Asp Glu Gly Gly Phe
                85                  90                  95

Thr Cys Phe Phe Arg Asp His Ser Tyr Gln Glu Ala Ala Met Glu
                100                 105                 110

Leu Lys Val Glu Asp Pro Phe Tyr Trp Val Ser Pro Gly Val Leu Val
            115                 120                 125

Leu Leu Ala Val Leu Pro Val Leu Leu Leu Gln Ile Thr Val Gly Leu
        130                 135                 140

Val Phe Leu Cys Leu Gln Tyr Arg Leu Arg Gly Lys Leu Arg Ala Glu
145                 150                 155                 160

Ile Glu Asn Leu His Arg Thr Phe Asp Pro His Phe Leu Arg Val Pro
                165                 170                 175

Cys Trp Lys Ile Thr Leu Phe Val Ile Val Pro Val Leu Gly Pro Leu
            180                 185                 190

Val Ala Leu Ile Ile Cys Tyr Asn Trp Leu His Arg Arg Leu Ala Gly
        195                 200                 205

Gln Phe Leu Glu Glu Leu Arg Asn Pro Phe
    210                 215

<210> SEQ ID NO 6
<211> LENGTH: 21
<212> TYPE: PRT
<213> ORGANISM: Homo sapiens

<400> SEQUENCE: 6

Tyr Arg Pro Pro Phe Ser Arg Val Val His Leu Tyr Arg Asn Gly Lys
1               5                   10                  15

Asp Gln Asp Gly Asp
            20

<210> SEQ ID NO 7
<211> LENGTH: 21
<212> TYPE: PRT
<213> ORGANISM: Mus musculus

<400> SEQUENCE: 7

Met Glu Val Gly Trp Tyr Arg Ser Pro Phe Ser Arg Val Val His Leu
1               5                   10                  15

Tyr Arg Asn Gly Lys
            20

<210> SEQ ID NO 8
<211> LENGTH: 15
<212> TYPE: PRT
<213> ORGANISM: Mus musculus

<400> SEQUENCE: 8

Arg Ser Pro Phe Ser Arg Val Val His Leu Tyr Arg Asn Gly Lys
1               5                   10                  15
```

MYELIN OLIGODENDROCYTE GLYCOPROTEIN (MOG) PEPTIDE

CROSS REFERENCE TO RELATED APPLICATIONS

This application is a continuation of U.S. patent application Ser. No. 14/760,493, filed on Jul. 13, 2015, now U.S. Pat. No. 9,862,751, issued Jan. 9, 2018, which is a U.S. National Phase Application of PCT/IB2014/058233, filed Jan. 1, 2014, which claims the priority benefit of Great Britain Patent Application No. 1300684.6, filed on Jan. 15, 2013, which is incorporated by reference in its entirety.

The present invention relates to peptides from myelin oligodendrocyte glycoprotein (MOG). In particular, the invention relates to peptides which comprise a portion of the region 40-60 of MOG which are capable of binding to an MHC molecule and being presented to a T-cell in vitro without antigen processing. The invention also relates to the use of such peptides in the treatment and/or prevention of a disease.

BACKGROUND

Multiple sclerosis (MS) is a chronic degenerative disease affecting the central nervous system, characterized by demyelination of nerve axons. MS may cause numerous physical and mental symptoms, and often progresses to both physical and cognitive disability. Disease onset usually occurs in young adults (20-40 yrs), is more common in women, and affects more than 1 million people around the world.

The disease course of MS is varied and may lie dormant or progress steadily over time. Several subtypes of MS have been described based on patterns of progression. A person with MS can suffer almost any neurological symptom or sign, including changes in sensation such as loss of sensitivity or tingling, pricking or numbness (hypoesthesia and paraesthesia), muscle weakness, clonus, muscle spasms, or difficulty in moving; difficulties with coordination and balance (ataxia); problems in speech (dysarthria) or swallowing (dysphagia), visual problems (nystagmus, optic neuritis including phosphenes, or diplopia), fatigue, acute or chronic pain, and bladder and bowel difficulties.

MS is currently believed to be an immune-mediated disorder in which the body's own immune system attacks and damages myelin.

There is no known cure for MS. Several current therapies have proven beneficial in restoring function after an attack (relapse), preventing or reducing the degree or frequency of new attacks (relapses), or preventing or reducing the extent of disability. However, many current MS therapies have been associated with adverse effects or are poorly tolerated. There is thus a need for alternative therapies for MS which are effective at treating MS and at alleviating or reducing the symptoms of MS.

SUMMARY OF THE INVENTION

The present inventors have identified a number of peptides derivable from myelin oligodendrocyte glycoprotein which can be presented by fixed antigen presenting cells to T-cells. These peptides may be useful in the prevention and/or treatment of demyelinating diseases such as multiple sclerosis.

In a first aspect, therefore, the present invention provides a peptide which is capable of binding to an MHC molecule in vitro and being presented to a T cell without antigen processing (i.e. an apitope), which comprises a portion of the region 40-60 of myelin oligodendrocyte glycoprotein (MOG).

The peptide may comprise a portion of the region 41-59 of myelin oligodendrocyte glycoprotein.

The peptide may be selected from the following myelin oligodendrocyte glycoprotein peptides: MOG 41-55, 43-57, 44-58 and 45-59.

The peptide may be MOG 41-55.

In a second aspect there is provided a peptide according to the first aspect of the invention for use in the treatment and/or prevention of a demyelinating disease.

In a third aspect, the present invention provides a pharmaceutical composition comprising one or more peptide(s) according to the first aspect of the invention.

In a fourth aspect the present invention provides a method for treating and/or preventing a demyelinating disease in a subject in need of same which comprises the step of administering a peptide according to the first aspect of the invention to the subject.

In a fifth aspect, the present invention relates to the use of a peptide according to the first aspect of the invention in the manufacture of a medicament for use in the prevention and/or treatment of a demyelinating disease.

In connection with the second, fourth and fifth aspects of the invention, the disease may be multiple sclerosis.

DETAILED DESCRIPTION

Figure 1:
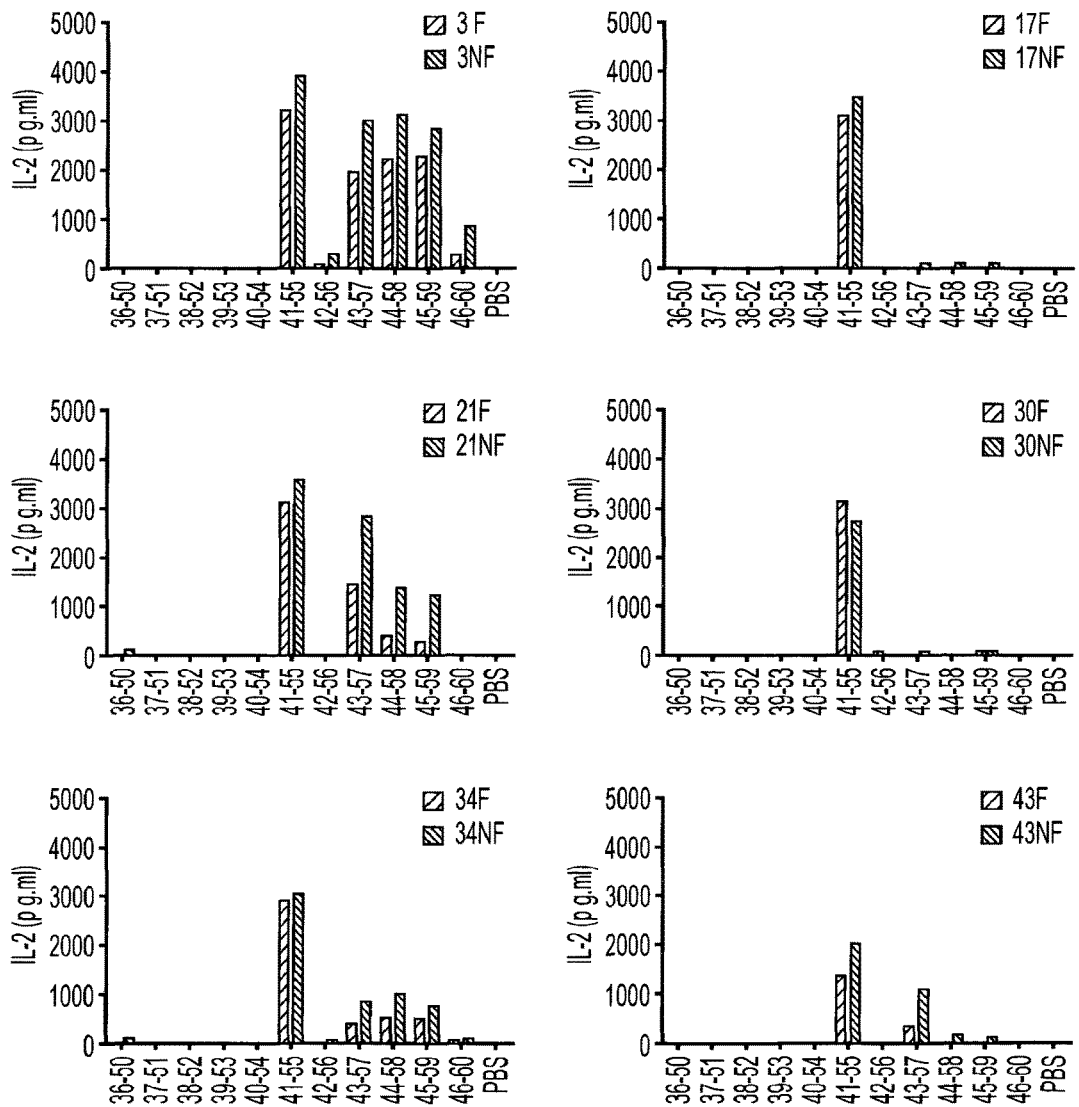
FIG. 1 is a graph to show the peptide specificity of various MOG-specific hybridoma clones.

In a first aspect, the present invention relates to a peptide.
Peptides

The term "peptide" is used in the normal sense to mean a series of residues, typically L-amino acids, connected one to the other typically by peptide bonds between the α-amino and carboxyl groups of adjacent amino acids The term includes modified peptides and synthetic peptide analogues.

A peptide of the present invention is of a length that is capable of binding to a major histocompatibility complex (MHC) class I or II molecule in vitro and being presented to a T cell without antigen processing. In other words the peptides are capable of binding directly into the peptide binding groove of the MHC molecule without requiring any trimming at one or both ends.

Peptides that bind to MHC class I molecules are typically 7 to 13, more usually 8 to 10 amino acids in length. The binding of the peptide is stabilised at its two ends by contacts between atoms in the main chain of the peptide and invariant sites in the peptide-binding groove of all MHC class I molecules. There are invariant sites at both ends of the groove which bind the amino and carboxy termini of the peptide. Variations in peptide length are accommodated by a kinking in the peptide backbone, often at proline or glycine residues that allow the required flexibility.

Peptides which bind to MHC class II molecules are typically between 8 and 20 amino acids in length, more usually between 10 and 17 amino acids in length. These peptides lie in an extended conformation along the MHC II peptide-binding groove which (unlike the MHC class I peptide-binding groove) is open at both ends. The peptide is held in place mainly by main-chain atom contacts with conserved residues that line the peptide-binding groove.

The peptide of the present invention may be made using chemical methods (Peptide Chemistry, A practical Textbook. Mikos Bodansky, Springer-Verlag, Berlin.). For example, peptides can be synthesized by solid phase techniques (Roberge J Y et al (1995) Science 269: 202-204), cleaved from the resin, and purified by preparative high performance liquid chromatography (e.g., Creighton (1983) Proteins Structures And Molecular Principles, WH Freeman and Co, New York N.Y.). Automated synthesis may be achieved, for example, using the ABI 43 1 A Peptide Synthesizer (Perkin Elmer) in accordance with the instructions provided by the manufacturer.

The peptide may alternatively be made by recombinant means, or by cleavage from a longer polypeptide. For example, the peptide may be obtained by cleavage from myelin basic protein. The composition of a peptide may be confirmed by amino acid analysis or sequencing (e.g., the Edman degradation procedure).

Myelin Oligodendrocyte Glycoprotein (MOG)

Myelin oligodendrocyte glycoprotein (MOG) is a type I integral membrane protein possessing a single extracellular Ig variable domain (Ig-V). The amino acid sequence of MOG is highly conserved among animal species (>90%), indicative of an important biological function. MOG is specifically expressed in the CNS on the outermost lamellae of the myelin sheath as well as the cell body and processes of oligodendrocytes.

The sequence of mature MOG (lacking the 29 amino acid signal peptide) is given below (SEQ ID NO: 5).

```
                                            SEQ ID NO: 5
GQFRVIGPRHPIRALVGDEVELPCRISPGKNATGMEVGWYRPPFSRVVHL

YRNGKDQDGDQAPEYRGRTELLKDAIGEGKVTLRIRNVRESDEGGFTCFF

RDHSYQEEAAMELKVEDPFYWVSPGVLVLLAVLPVLLLQITVGLVFLCLQ

YRLRGKLRAEIENLHRTFDPHFLRVPCWKITLFVIVPVLGPLVALIICYN

WLHRRLACQELEELRNPF
```

The peptide of the invention is derivable from region 40-60 of myelin oligodendrocyte glycoprotein (MOG). The peptide may be derivable from a fragment of the antigen which arises by natural processing of the antigen by an antigen presenting cell.

Region 40-60 of MOG has the following sequence:

```
                                            SEQ ID NO: 6
                    YRPPFSRVVHLYRNGKDQDGD
```

The peptide may comprise the minimal epitope from the following peptides: MOG 41-55, 43-57, 44-58 and 45-59.

The sequences of MOG 41-55, 43-57, 44-58 and 45-59 are:

```
                                          (SEQ ID NO: 1)
          MOG 41-55: RPPFSRVVHLYRNGK (SEQ ID NO: 2)
          MOG 43-57: PFSRVVHLYRNGKDQ (SEQ ID NO: 3)
          MOG 44-58: FSRVVHLYRNGKDQD (SEQ ID NO: 4)
          MOG 45-59: SRVVHLYRNGKDQDG
```

The peptide may comprise the minimal epitope from MOG 41-55. The peptide may consist of MOG 41-55.

Apitopes

In an adaptive immune response, T lymphocytes are capable of recognising internal epitopes of a protein antigen. Antigen presenting cells (APC) take up protein antigens and degrade them into short peptide fragments. A peptide may bind to a major histocompatibility complex (MHC) class I or II molecule inside the cell and be carried to the cell surface. When presented at the cell surface in conjunction with an MHC molecule, the peptide may be recognised by a T cell (via the T cell receptor (TCR)), in which case the peptide is a T cell epitope.

T cell epitopes play a central role in the adaptive immune response to any antigen, whether self or foreign. The central role played by T cell epitopes in hypersensitivity diseases (which include allergy, autoimmune diseases and transplant rejection) has been demonstrated through the use of experimental models. It is possible to induce inflammatory or allergic diseases by injection of synthetic peptides (based on the structure of T cell epitopes) in combination with adjuvant.

By contrast, it has been shown to be possible to induce immunological tolerance towards particular peptide epitopes by administration of peptide epitopes in soluble form. Administration of soluble peptide antigens has been demonstrated as an effective means of inhibiting disease in experimental autoimmune encephalomyelitis (EAE—a model for multiple sclerosis (MS)) (Metzler and Wraith (1993) Int. Immunol. 5:1159-1165; Liu and Wraith (1995) Int. Immunol. 7:1255-1263; Anderton and Wraith (1998) Eur. J. Immunol. 28:1251-1261); and experimental models of arthritis, diabetes, and uveoretinitis (reviewed in Anderton and Wraith (1998) as above). This has also been demonstrated as a means of treating an ongoing disease in EAE (Anderton and Wraith (1998) as above).

The use of tolerogenic peptides to treat or prevent disease has attracted considerable attention. One reason for this is that it has been shown that certain tolerogenic epitopes can down-regulate responses of T cells for distinct antigens within the same tissue. This phenomenon, known as "bystander suppression" means that it should be possible to induce tolerance to more than one epitope (preferably all epitopes) within a given antigen, and to more than one antigen for a given disease, using a particular tolerogenic peptide (Anderton and Wraith (1998) as above). This would obviate the need to identify all of the pathogenic antigens within a particular disease.

Peptides are also a favourable option for therapy because of their relatively low cost and the fact that peptide analogues can be produced with altered immunological properties. Peptides may thus be modified to alter their interactions with either MHC or TCR.

One possible problem with this approach is that it has been shown that not all peptides which act as T cell epitopes are capable of inducing tolerance. The myelin basic protein (MBP) peptide 89-101 is an immunodominant antigen after immunisation and is also a very effective immunogen both in terms of priming for T cell reactivity and induction of EAE. However, this peptide has been shown to be ineffective at inducing tolerance when administered in solution (Anderton and Wraith (1998), as above).

A number of explanations for the observed hierarchy in the ability of T cell epitopes to induce tolerance have been proposed (reviewed in Anderton and Wraith (1998) as above). In particular, it has been proposed that there is a correlation between the affinity of the peptide for the MHC and tolerogenicity (Liu and Wraith (1995) as above), but this does not tally with some of the observations. For example, MBP [89-101], which is not tolerogenic, binds to I-A$^S$ with relatively high affinity. It is thus not straightforward to predict which peptides will induce tolerance.

The present inventors have shown that if a peptide epitope is of an appropriate size to be presented by immature APC without antigen processing, it can induce immunological tolerance (International patent application number PCT/GB01/03702). The observation that some T cell epitopes are tolerogenic and others are incapable of inducing tolerance can therefore be explained by the fact that some epitopes require antigen processing before they are capable of being presented by an MHC molecule. These epitopes which require further processing do not induce tolerance when administered in a soluble form, despite their capacity to induce disease when injected in combination with adjuvant.

The epitopes which do not require further processing are capable of inducing tolerance, and have been termed "apitopes" (Antigen Processing Independent epiTOPES) by the inventors.

Antigen Processing Independent Presentation Systems (APIPS)

The peptides of the present invention are capable of binding to an MHC molecule in vitro and being presented to a T cell without antigen processing.

It is possible to test whether a peptide is capable of binding to an MHC molecule without antigen processing using a "processing free" system. Such a system should be capable of presenting antigen via MHC molecules to T cells, but incapable of processing antigen. Thus peptides may be tested for their capacity to bind to an MHC molecule in vitro and being presented to a T cell without antigen processing using an antigen processing independent presentation system (APIPS).

Examples of APIPS include:
a) fixed APC (with or without antibodies to CD28);
b) Lipid membranes containing Class I or II MHC molecules (with or without antibodies to CD28); and
c) purified natural or recombinant MHC in plate-bound form (with or without antibodies to CD28).

It is known to use fixed APC to investigate T cell responses, for example in studies to investigate the minimal epitope within a polypeptide, by measuring the response to truncated peptides (Fairchild et al (1996) Int. Immunol. 8:1035-1043). APC may be fixed using, for example formaldehyde (usually paraformaldehyde) or glutaraldehyde.

Lipid membranes (which may be planar membranes or liposomes) may be prepared using artificial lipids or may be plasma membrane/microsomal fractions from APC.

In use, the APIPS may be applied to the wells of a tissue culture plate. Peptide antigens are then added and binding of the peptide to the MHC portion of the APIPS is detected by addition of selected T cell lines or clones. Activation of the T cell line or clone may be measured by any of the methods known in the art, for example via $^3$H-thymidine incorporation or cytokine secretion.

If a peptide is capable of being presented to a T cell by an APIPS, then it is capable of binding to the MHC molecule without antigen processing, and is an apitope.

Tolerance

The peptides of the present invention are capable of inducing tolerance to myelin oligodendrocyte glycoprotein (MOG).

As used herein, the term "tolerogenic" means capable of inducing tolerance.

Tolerance is the failure to respond to an antigen. Tolerance to self antigens is an essential feature of the immune system, when this is lost, autoimmune disease can result. The adaptive immune system must maintain the capacity to respond to an enormous variety of infectious agents while avoiding autoimmune attack of the self antigens contained within its own tissues. This is controlled to a large extent by the sensitivity of immature T lymphocytes to apoptotic cell death in the thymus (central tolerance). However, not all self antigens are detected in the thymus, so death of self-reactive thymocytes remains incomplete. There are thus also mechanisms by which tolerance may be acquired by mature self-reactive T lymphocytes in the peripheral tissues (peripheral tolerance). A review of the mechanisms of central and peripheral tolerance is given in Anderton et al (1999) (*Immunological Reviews* 169:123-137).

Tolerance may result from or be characterised by the induction of anergy in at least a portion of CD4+ T cells. In order to activate a T cell, a peptide must associate with a "professional" APC capable of delivering two signals to T cells. The first signal (signal 1) is delivered by the MHC-peptide complex on the cell surface of the APC and is received by the T cell via the TCR. The second signal (signal 2) is delivered by costimulatory molecules on the surface of the APC, such as CD80 and CD86, and received by CD28 on the surface of the T cell. It is thought that when a T cell receives signal 1 in the absence of signal 2, it is not activated and, in fact, becomes anergic. Anergic T cells are refractory to subsequent antigenic challenge, and may be capable of suppressing other immune responses. Anergic T cells are thought to be involved in mediating T cell tolerance.

Peptides which require processing before they can be presented in conjunction with MHC molecules do not induce tolerance because they have to be handled by mature antigen presenting cells. Mature antigen presenting cells (such as macrophages, B cells and dendritic cells) are capable of antigen processing, but also of delivering both signals 1 and 2 to a T cell, leading to T cell activation. Apitopes, on the other hand, will be able to bind class II MHC on immature APC. Thus they will be presented to T cells without costimulation, leading to T cell anergy and tolerance.

Of course, apitopes are also capable of binding to MHC molecules at the cell surface of mature APC. However, the immune system contains a greater abundance of immature than mature APC (it has been suggested that less than 10% of dendritic cells are activated, Summers et al. (2001) Am.

J. Pathol. 159: 285-295). The default position to an apitope will therefore be anergy/tolerance, rather than activation.

It has been shown that, when tolerance is induced by peptide inhalation, the capacity of antigen-specific CD4+ T cells to proliferate is reduced. Also, the production of IL-2, IFN-γ and IL-4 production by these cells is down-regulated, but production of IL-10 is increased. Neutralisation of IL-10 in mice in a state of peptide-induced tolerance has been shown to restore completely susceptibility to disease. It has been proposed that a population of regulatory cells persist in the tolerant state which produce IL-10 and mediate immune regulation (Burkhart et al (1999) Int. Immunol. 11:1625-1634).

The induction of tolerance can therefore be monitored by various techniques including:
(a) reduced susceptibility to contract the disease for which the peptide is a target epitope in vivo;
(b) the induction of anergy in CD4+ T cells (which can be detected by subsequent challenge with antigen in vitro);
(c) changes in the CD4+ T cell population, including
  (i) reduction in proliferation;
  (ii) down-regulation in the production of IL-2, IFN-γ and IL-4; and
  (iii) increase in the production of IL-10.

Target Diseases

The peptide of the invention may be used in the treatment and/or prevention of a disease.

The disease may be a demyelinating diseases, such as adrenoleukodystrophy, vanishing white matter disease, or multiple sclerosis (MS).

The peptides of the present invention are particularly useful in the treatment and/or prevention of multiple sclerosis (MS). Multiple sclerosis (MS) is a chronic inflammatory disease characterised by multiple demyelinating lesions disseminated throughout the CNS white matter and occurring at various sites and times (McFarlin and McFarland, 1982 New England J. Medicine 307:1183-1188 and 1246-1251). MS is thought to be mediated by autoreactive T cells.

Pharmaceutical Composition

In a second aspect, the present invention relates to a pharmaceutical composition comprising one or more peptide(s) of the first aspect of the invention.

The present inventors predict that, despite "bystander suppression" it may be necessary to target a number of different T cell clones in order to induce tolerance effectively. Hence a plurality of peptides may be administered to an individual in order to prevent or treat a disease.

The pharmaceutical composition may, for example comprise between 1 and 20 apitopes, for example 1 to 15, 2 to 8 or 4 to 6 apitopes.

Where there are two or more apitopes, the pharmaceutical composition may be in the form of a kit, in which some or each of the apitopes are provided separately for simultaneous, separate or sequential administration.

Alternatively (or in addition) if the pharmaceutical composition (or any part thereof) is to be administered in multiple doses, each dose may be packaged separately.

The pharmaceutical composition may comprise a therapeutically or prophylactically effective amount of the or each apitope and optionally a pharmaceutically acceptable carrier, diluent or excipient.

Also, in the pharmaceutical compositions of the present invention, the or each apitope may be admixed with any suitable binder(s), lubricant(s), suspending agent(s), coating agent(s), or solubilising agent(s).

Administration

The peptide may be administered in soluble form in the absence of adjuvant.

The peptide may be administered by a mucosal route.

Studies have shown that peptide, when given in soluble form intraperitoneally (i.p.), intravenously (i.v.) or intranasally (i.n.) or orally can induce T cell tolerance (Anderton and Wraith (1998) as above; Liu and Wraith (1995) as above; Metzler and Wraith (1999) Immunology 97:257-263).

The peptide may be administered intranasally.

Studies in mice have demonstrated that the duration of peptide administration required to induce tolerance depends on the precursor frequency of T cells in the recipient (Burkhart et al (1999) as above). In many experimental studies, it has been shown that repeated doses of peptide are required to induce tolerance (Burkhart et al (1999) as above). The exact dose and number of doses of peptide will therefore depend on the individual, however, in a preferred embodiment a plurality of doses is administered.

If a plurality of peptides is administered simultaneously, they may be in the form of a "cocktail" which is suitable for administration in single or multiple doses. Alternatively it may be preferable to give multiple doses but vary the relative concentrations of the peptides between doses.

In a preferred embodiment a "dose escalation" protocol may be followed, where a plurality of doses is given to the patient in ascending concentrations. Such an approach has been used, for example, for phospholipase A2 peptides in immunotherapeutic applications against bee venom allergy (Müller et al (1998) J. Allergy Clin Immunol. 101:747-754 and Akdis et al (1998) J. Clin. Invest. 102:98-106).

EXAMPLES

The following examples serve to illustrate the present invention, but should not be construed as a limitation thereof. The invention particularly relates to the specific embodiments described in these examples Example 1—Identification of Apitopes within Myelin Oligodendrocyte Glycoprotein (MOG)

Materials and Methods

Antigens

A nucleic acid sequence encoding the 125-amino acid N-terminal portion of human MOG, which represents the extracellular domain, was cloned into a bacterial expression vector (pET system). This recombinant human MOG extracellular domain (rhMOG$_{ED}$) was expressed in a bacterial system as a fusion protein with a His tag on the C-terminus.

A panel of 15-mer overlapping peptides spanning rhMOG$_{ED}$ was synthesised using standard F-moc chemistry. The 15mers peptides were displaced by 5aa and overlapping by 10aa.

Generation of T Cell Clones

MOG-specific hybridoma T cell clones were generated by immunisation of DR2+ mice. DR2+ mice were immunised with either a pool of MOG overlapping peptides or rhMOG$_{ED}$ in complete Freunds adjuvant (CFA). After 10 days, the spleen and draining lymph nodes were removed, CD4+ T cells were purified and restimulated with antigen/CFA in vitro. A week later, T cells were restimulated in vitro with antigen to increase the number of activated antigen-specific cells.

After 3 days, activated T cells were fused with the thymoma cell line BW 5147. Hybridoma clones were then selected using HAT selection medium and screened for peptide specificity by IL-2 ELISA.

Proliferation Assay

Live or p-formaldehyde fixed Mgar (HLA-DR2+ve) cells were incubated with peptides in serum or in serum alone, together with T cells for 48 hours. The T cell proliferative response was measured by IL-2 production.

Results

The response of various MOG-specific hybridoma clones to presentation of nested MOG peptides is shown in FIG. 1. The peptide MOG 41-55 ("ROK5") was defined as an apitope as it could be presented by fixed APC to T cells without further processing. A detailed study was then carried out using overlapping peptides in the region 25-60, using peptides that are displaced by one amino acid. The peptides MOG 41-55, 43-57, 44-58 and 45-59 were identified as apitopes (FIG. 1).

The sequences of these peptides are given in Table 1.

TABLE 1

Sequence of MOG peptides identified as apitopes

| Peptide | MOG | Amino acid sequence |
|---------|-----|---------------------|
| ROK5 | MOG 41-55 | RPPFSRVVHLYRNGK (SEQ ID NO: 1) |
| ROK19 | MOG 43-57 | PFSRVVHLYRNGKDQ (SEQ ID NO: 2) |
| ROK20 | MOG 44-58 | FSRVVHLYRNGKDQD (SEQ ID NO: 3) |
| ROK21 | MOG 45-59 | SRVVHLYRNGKDQDG (SEQ ID NO: 4) |

Example 2—Ex Vivo Tolerance Assay

In order to determine whether the peptides identified as apitopes are capable of inducing tolerance to antigen, an ex vivo study was performed. HLA-DR2 transgenic mice were immunised with either 100 µg ROK5 (MOG 41-55), 100 µg MOG 35-55 or PBS on days −8, −4 and −2. On day 0, mice were challenged with 100 µg MOG 35-55 by injection in the tail base in combination with CFA.

On day 10, splenocytes and draining lymph nodes were harvested and their respective cell populations isolated and a recall proliferation assay was set up with MOG 35-55. Cells from individual mice were treated separately and data is plotted separately in FIG. 2. For the recall response cells were treated ex vivo with a dose range of MOG35-55 (100, 10, 1, 0.1, 0.01, 0 µg) and proliferation via $^3$H-thymidine incorporation determined. Stimulation index (compared to proliferation with no antigen) was calculated for each condition.

Figure 2:
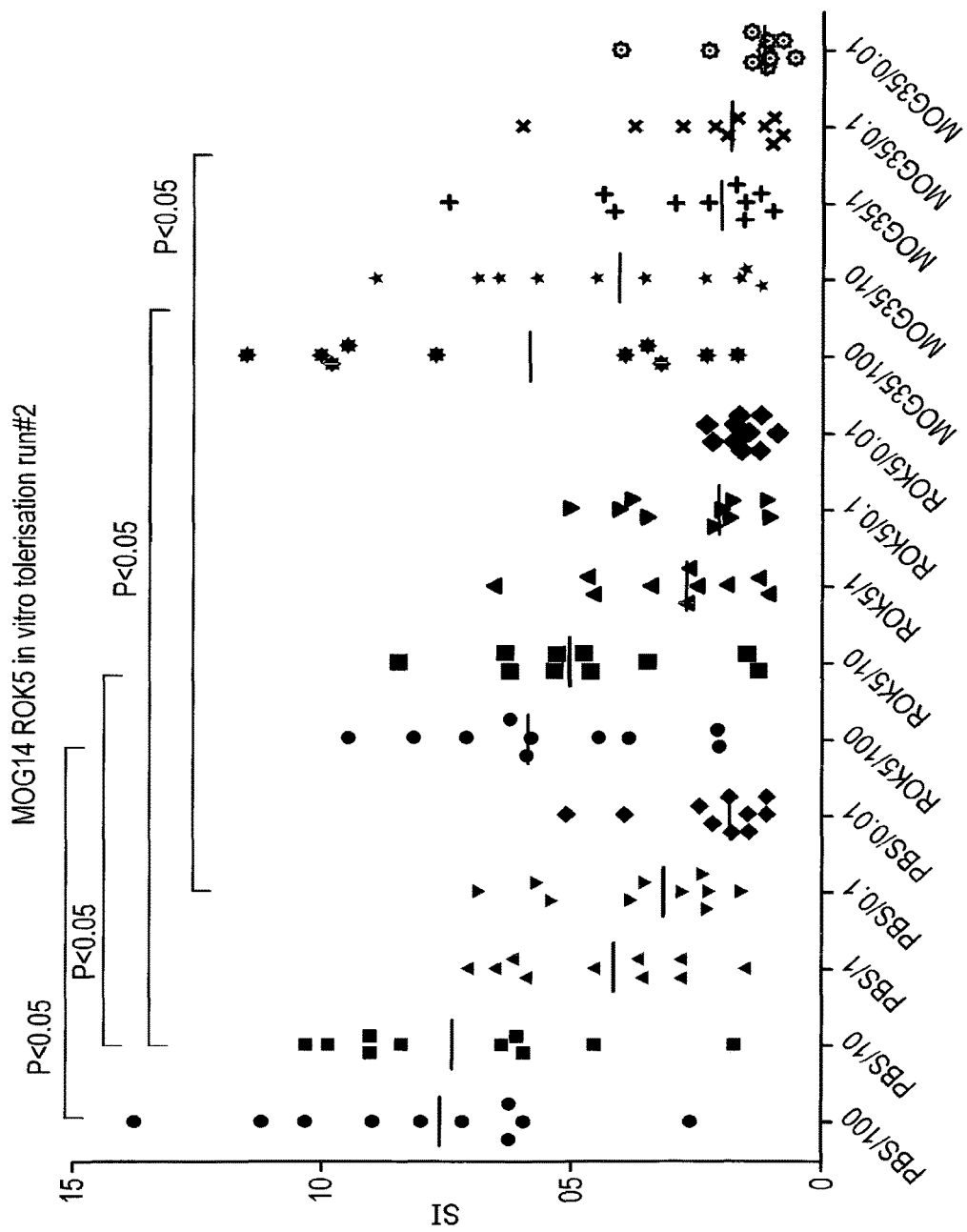
FIG. 2 shows the results of a recall proliferation assay to test the effect of treatment of mice with ROK5 (MOG 41-55) prior to immunisation with MOG35-55 followed by an in vitro recall with MOG35-55.

As shown in FIG. 2, ROK5 (MOG 41-55) was able to suppress the immune response to challenge with MOG 35-55.

Figure 3:
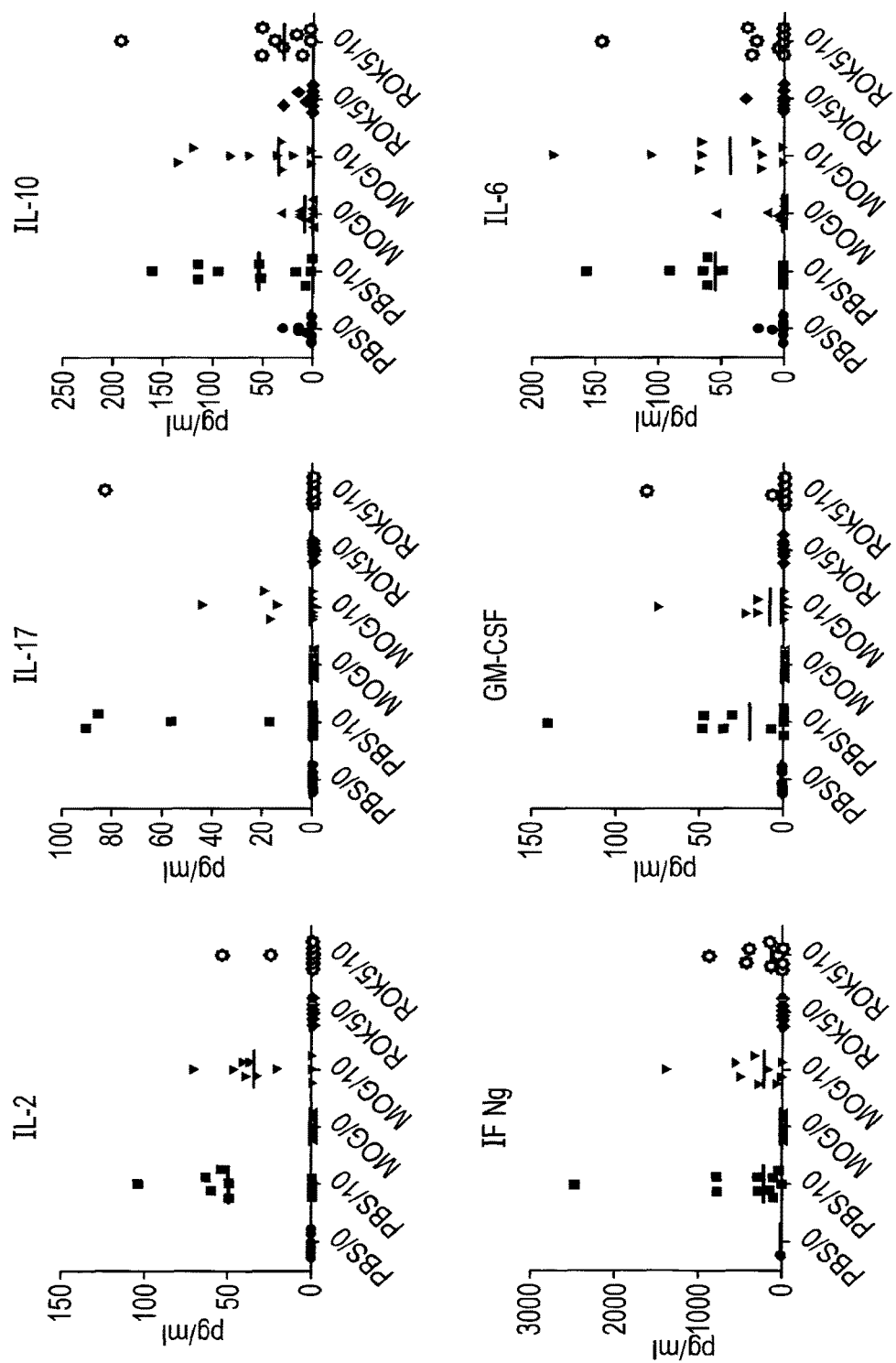
FIG. 3 shows the cytokine profiles from supernatants from splenocytes from mice pretreated in vivo with ROK5 or PBS and immunisation with MOG35-55 followed by an in vitro recall with MOG35-55.

The effect of ROK5 pre-treatment on various cytokine profiles was also investigated. As shown in FIG. 3, the production of IFNγ, IL-2, GM-CSF, IL6 by splenocytes are clearly affected by the ROK5 pretreatment.

Example 3—ROK5 EAE Prevention

EAE (experimental autoimmune encephalomyelitis) is a widely studied model of MS, and can be induced in a wide range of genetically susceptible laboratory animal species (including rodents and primates) by immunization with myelin or myelin components (including MOG) in strong adjuvants.

To test the capacity of ROK5 to prevent MOG-induced EAE in HLA-DR2 transgenic mice, the disease model was established in this strain of mice. To induce the disease, the encephalitogenic MOG peptide, mouse MOG 35-55 (mMOG35-55) was used. Then, ROK5 was tested in EAE prevention experiments as follows:

Experiment 1: with 3 ROK5 dose pre-treatments, followed by immunisation with mMOG35-55.

Experiment 2: with 5 ROK5 dose pre-treatments, followed by immunisation with mMOG35-55.

In each experiment, 10 mice were used per group.

Peptides Sequences:

```
                                          (SEQ ID NO: 7)
mMOG35-55: MEVGWYRSPFSRVVHLYRNGK (SEQ ID NO: 1)
hROK5 (41-55): RPPFSRVVHLYRNGK (SEQ ID NO: 8)
mROK5 (41-55): RSPFSRVVHLYRNGK
```

Human and mouse MOG differ by an amino-acid substitution in position 42, substitution of a proline for a serine. Both MOG35-55 peptides are immunogenic, but the mouse MOG35-55 is more encephalitogenic, therefore mouse MOG35-55 was chosen to induce EAE in the model.

Figure 4:
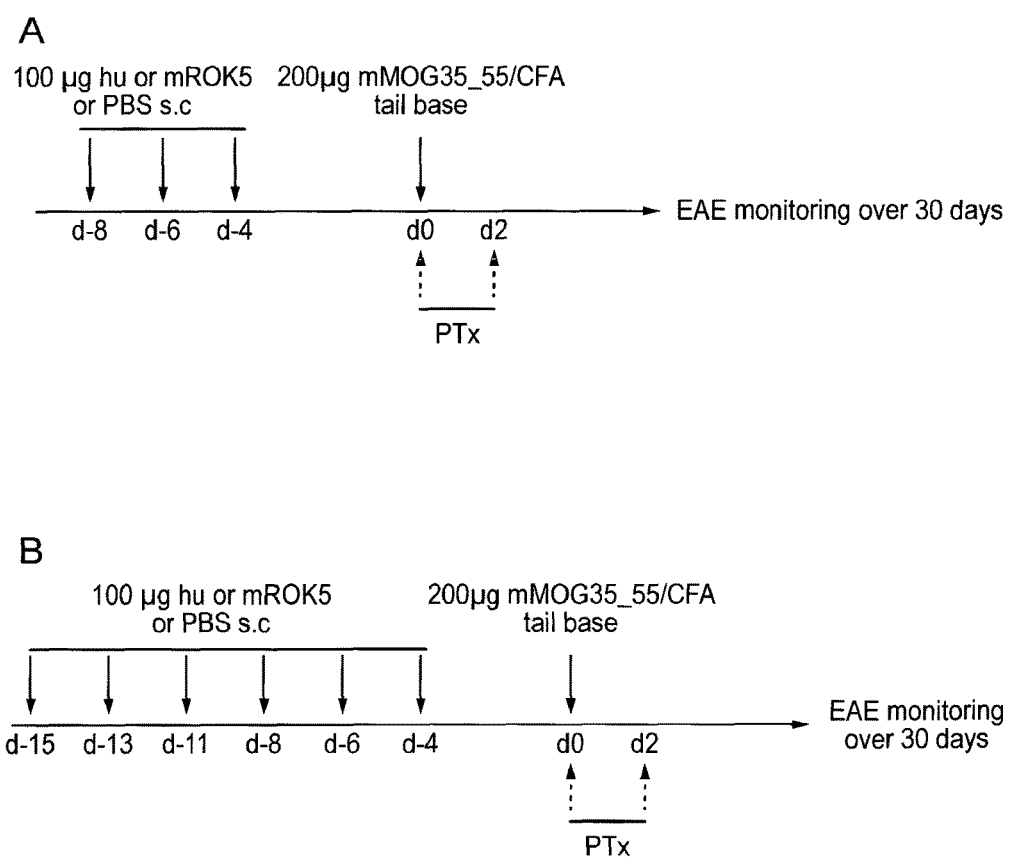
FIG. 4 schematically illustrates the in vivo EAE prevention protocols.

In vivo EAE prevention protocols are described in FIGS. 4A and 4B.

MOG-Induced EAE Model:

Two groups of DR2 transgenic mice were setup, at day zero, animals (n=7) in group "100 µg" received 100 µg mMOG35-55 in Complete Freund's Adjuvant (CFA) (100 µl, s.c., base of the tail injection), animals (n=8) in group "200 µg" received 200 µg mMOG35-55 in CFA. At day zero and day2, all animals received an injection of Pertussis toxin (200 ng in PBS, i.p.). Every day, clinical EAE was scored and animal body weight measured.

Figure 5:
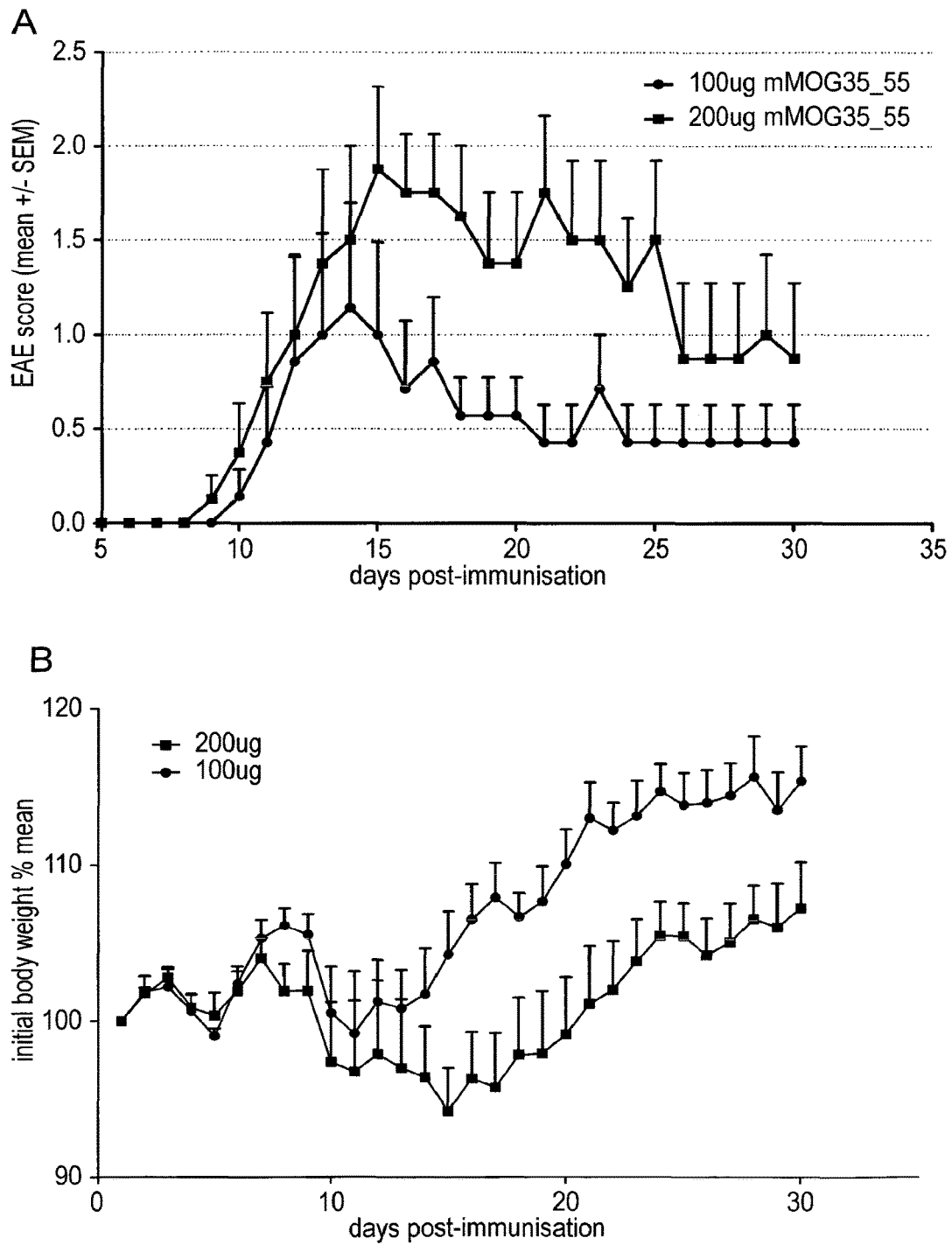
FIG. 5 shows that the peptide MOG35-55 induces EAE in a murine model.

As shown in FIGS. 5A, 5B and table 2 below, both doses of mMOG35-55 can induce EAE with a good incidence.

TABLE 2

| Group | Incidence | Mean day of onset |
|-------|-----------|-------------------|
| 100 ug | 4/7 | 12.25 |
| 200 ug | 7/8 | 12 |

ROK5 EAE Prevention Experiments:

On this basis, the ability of ROK5 to prevent MOG-induced EAE was tested.

A/First Experiment

A first experiment was performed where animals were pretreated 3 times (3 days apart) with either mouse ROK5, human ROK5 or PBS, 100 µg in 100 µl in CFA (s.c. injection in the flank), then all animals were immunised with 200 µg mMOG35-55 in CFA (s.c. injection at the base of the tail) and with 200 ng Pertussis toxin (200 ng in PBS, i.p.) at day zero and day 2.

Figure 6:
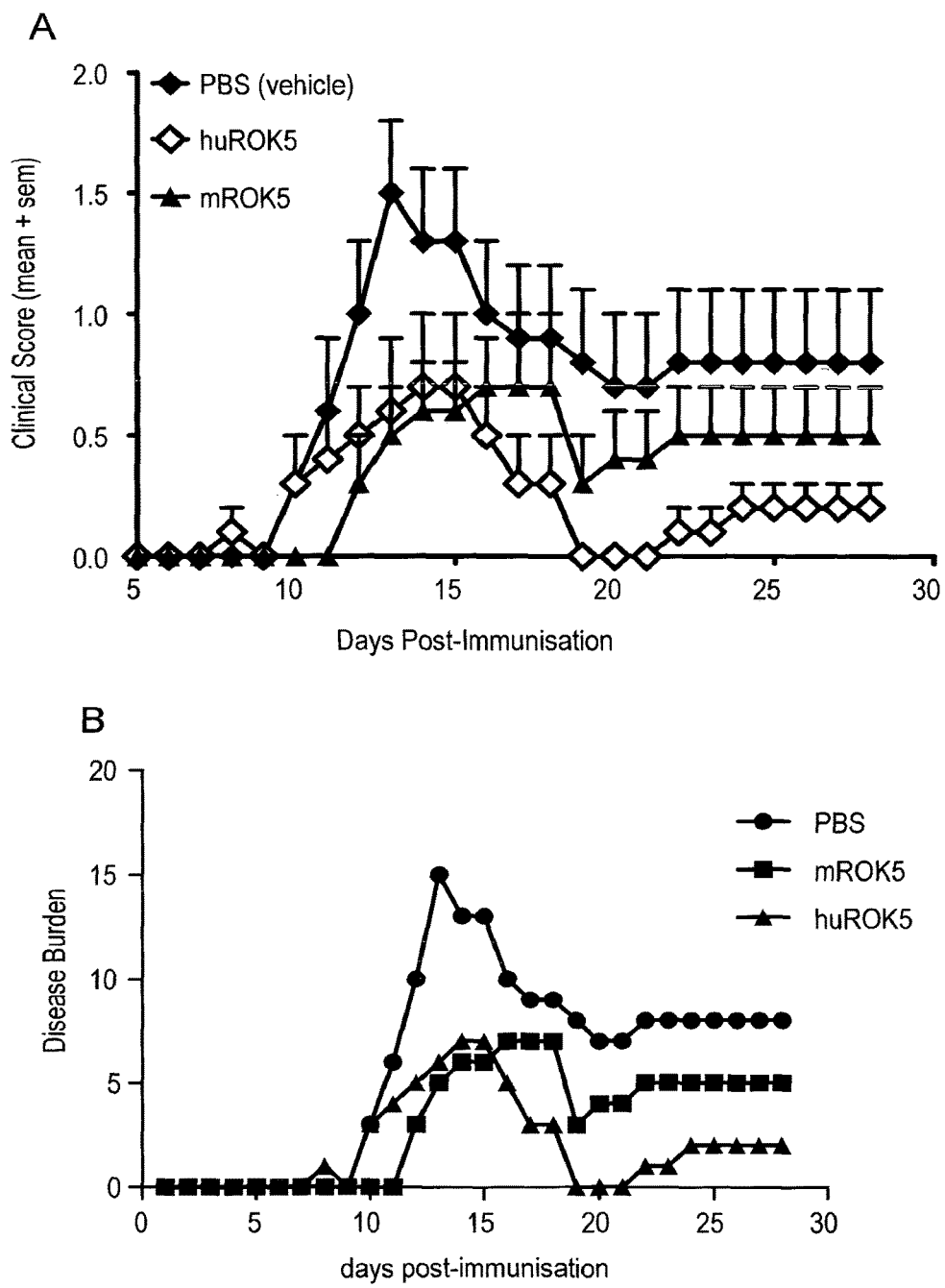
FIG. 6 shows that both mouse and human ROK5 apitopes can reduce the severity of the disease induced by MOG35-55.

Every day, clinical EAE was scored and animal body weight measured. FIG. 6 shows that both mouse and human ROK5 apitope can reduce the severity of the disease induced by MOG. Interestingly, human ROK5 is more efficient.

As shown in FIGS. 6A and 6B, experiment 1 shows that both mouse and human ROK5 apitopes can reduce the severity of the disease induced by MOG35-55.

B/Second Experiment

A second experiment was performed where animals were pretreated 5 times (3 days apart) with either human ROK5 or PBS, 100 µg in 100 µl in CFA (s.c. injection in the flank), then all animals were immunised with 200 µg mMOG35-55 in CFA (s.c. injection at the base of the tail) and with 200 ng Pertussis toxin (200 ng in PBS, i.p.) at day zero and day 2. Every day, clinical EAE was scored.

Figure 7:
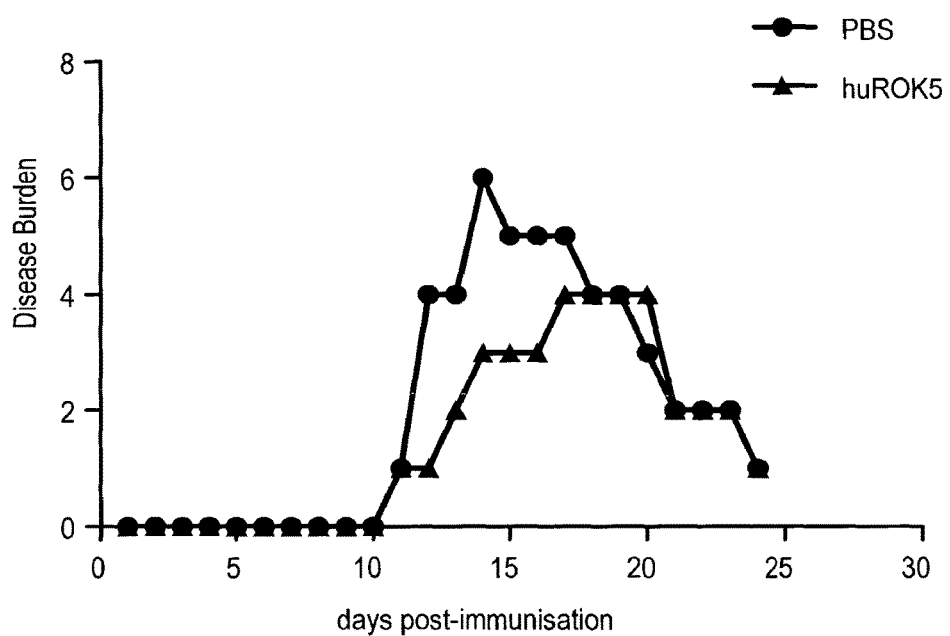
FIG. 7 shows that huROK5 reduced the severity of disease and caused a delay in the peak of disease burden.

In Experiment 2 (FIG. 7), huROK5 reduced the severity of disease and caused a delay in the peak of disease burden.

As a conclusion, Human ROK5 apitope was able to reduce disease severity in both EAE experiments.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or molecular biology or related fields are intended to be covered by the present invention. All publications mentioned in the above specification are herein incorporated by reference.

The invention claimed is:

1. A peptide which is capable of binding to an MHC molecule in vitro and being presented to a T cell without antigen processing, which is selected from the following myelin oligodendrocyte glycoprotein (MOG) peptides: MOG 44-58 and MOG 45-59.

* * * * *